United States Patent [19]

Singh

[11] 4,069,105

[45] Jan. 17, 1978

[54] LIDOCAINE ANTIGENS AND ANTIBODIES

[75] Inventor: Prithipal Singh, Santa Clara, Calif.

[73] Assignee: Syva Company, Palo Alto, Calif.

[21] Appl. No.: 775,658

[22] Filed: Mar. 3, 1977

[51] Int. Cl.$^2$ .............................................. C07G 7/00
[52] U.S. Cl. .................................... 195/63; 23/230 B; 195/68; 195/103.5 R; 260/78 A; 260/112 B; 260/112 R; 260/121; 424/12; 424/85; 424/88
[58] Field of Search ............... 195/63, 68; 260/112 R, 260/112 B, 121, 78 A; 424/12, 85

[56] References Cited

U.S. PATENT DOCUMENTS

| | | | |
|---|---|---|---|
| 3,690,834 | 9/1972 | Goldstein et al. | 23/230 |
| 3,817,837 | 6/1974 | Rubenstein et al. | 195/63 |
| 3,843,696 | 10/1974 | Wagner et al. | 260/112 B |
| 3,875,011 | 4/1975 | Rubenstein et al. | 195/103.5 R |
| 3,878,187 | 4/1975 | Schneider et al. | 260/112 R |
| 3,888,866 | 6/1975 | Leute et al. | 424/12 X |
| 3,966,556 | 6/1976 | Rubenstein et al. | 195/63 |
| 4,026,879 | 5/1977 | Spector | 260/112 R |

OTHER PUBLICATIONS

Acta Chem. Scand. 13, (1959), Dahibom et al., pp. 1145–1148.

*Primary Examiner*—Howard E. Schain
*Attorney, Agent, or Firm*—Townsend and Townsend

[57] ABSTRACT

Derivatives of anesthetics involving anilides, lidocaine being illustrative, are provided, having an annular amino group. A difunctional linking group is provided, which provides a link to the annular amino group and an antigen, with the resulting conjugate being employed for the preparation of antibodies. The antibodies find particular use in competitive protein binding assays. Conjugates to enzymes are prepared which find particular use in homogeneous enzyme immunoassays.

24 Claims, No Drawings

LIDOCAINE ANTIGENS AND ANTIBODIES

BACKGROUND OF THE INVENTION

1. Field of the Invention

There is increasing concern with the manner in which drugs are administered. Since in many instances, the effectiveness of the drug is directly related to the concentration of the drug in the bloodstream, both the manner and amount of the drug which is administered, affects the blood level of the drug during an extended period of time. The rate at which the desired blood level is achieved or exceeded will depend upon the nature of the drug, the manner of administration, the dosage, as well of the rate of metabolism. The rate at which a drug will enter the blood stream when administered other than intravenously and the rate at which the drug is metabolized varies widely with individuals. Furthermore, the level of effectiveness will also vary widely with individuals.

It is therefore desirable when administering drugs to ascertain the individual's level of effectiveness, the rate at which this level is achieved at a particular dosage and the time for which the level is maintained. In this manner, the amount of drug which is administered can then be carefully monitored to maintain the desired level. In this way, effectiveness can be assured and side effects minimized.

In order to monitor a drug in a physiological fluid, it is necessary to have sensitive tests which enable the rapid determination of the drug as distinct from any ineffectual metabolites. Thus, the test must clearly distinguish between the drug of interest and compounds of very similar structure. In competitive protein binding assays, antibodies are employed which are prepared by means of antigenic conjugates of derivatives of the drug of interest. In order for the antibodies to be effective, they must be produced in high titer, have a strong binding constant to the drug of interest, and weakly bind to compounds of similar structure.

There is also a need for a reagent which provides a measureable signal related to the amount of drug present in the assay medium. Where antibodies are involved, the reagent must effectively compete with the drug for antibody binding in a reproducible manner and provide for significant changes in the signal with small changes in the drug concentration, over the concentraion range of interest.

Other considerations for a reagent are that it is not affected by materials present in the unknown sample to be assayed or any interfering materials may be removed, an easily determinable signal is obtained, the reagent is stable under the assay condition and has a good storage life and the reagent is readily recognizable by the antibodies for the drug.

2. Brief Description of the Prior Art

Descriptions of competitive protein binding assays may be found in U.S. Pat. Nos. 3,817,837, 3,850,752, 3,690,834, and in an article by Murphy, J. Clin. Endocr. 27 973(1967). Preparation of antigenic conjugates and antibodies for a number of different drugs may be found in U.S. Pat. Nos. 3,888,866, 3,766,162, 3,843,696 and 3,878,187. U.S. Pat. No. 3,875,011 discloses glucose-6-phosphate dehydrogenase conjugates for use in homogeneous enzyme immunoassays. Dahlborn et al, Acta Chem. Scand. 13, 1145(1959) teaches the preparation of 4-amino-2,6-dimethyl-γ-dimethylaminoacetanilide.

SUMMARY OF THE INVENTION

Drugs having an anilide functionality are modified by introducing an amino group bonded to an annular carbon atom and the drug then linked by a linking group through the amino group to an antigenic compound, normally a poly(amino acid), or enzyme. Particularly, difunctional linking groups are employed which are capable of reacting with amino groups in stepwise fashion. Specifically, lidocaine is provided having an annular amino group and reacted with a dibasic carboxylic acid to provide an amic acid which is then reacted with available amino functionalities of a polypeptide.

DESCRIPTION OF THE SPECIFIC EMBODIMENTS

Drugs having an anilide functionality are conjugated through an annular amino substituent to antigens to provide an antigenic conjugate for the production of antibodies to the subject drug. The drugs of interest are N-substituted glycine anilides, wherein the nitrogen of the glycine is disubstituted with alkyl groups of from 1 to 4, usually 1 to 2 carbon atoms or an alkylene chain and an alkyl group, there being from 0 to 2, usually 1 to 2 lower alkyl substituents on the anilide ring. The linking group modified drugs are normally of from 12 to 30 carbon atoms and have a meta- or para- amino group for linking to the poly(amino acid) or other antigenic compound.

By poly(amino acid) is intended polypeptides and proteins, including any prosthetic groups or other polymeric compositions e.g. polysaccharides and nuclei acids. While polysaccharides may also be antigenic, for the most part poly(amino acids) are employed for inducing the formation of antibodies to haptens.

For the most part, the compounds of this invention have the following formula:

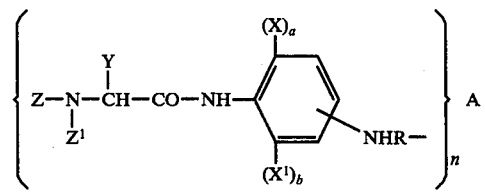

wherein:
X and X¹ are methyl;
a and b are 0 are 1, the sum of a + b being at least 1;
Y is hydrogen, methyl, or may be taken together with Z to form a 6 membered ring with the carbon and nitrogen atoms to which Y and Z are respectively attached;
Z and Z¹ are the same or different and are alkyl of from 1 to 4 carbon atoms, particularly methyl, ethyl and n-butyl, preferably being ethyl, when Z and Z¹ are the same, or Z may be taken together with Y to form a six membered ring as indicated above;
the amino groups bonded to the aromatic ring are separated by from 3 to 4 carbon atoms;
R is a linking group of from 1 to 8 carbon atoms having from 1 to 4 heteroatoms, which are oxygen, nitrogen and sulfur, wherein the oxygen is present as oxy or nonoxocarbonyl, particularly the latter, nitrogen is present as tertiary amino, amido or imino and sulfur is present as thioether or thiono;

and having from 0 to 1 site of ethylenic unsaturation;

A is a poly(amino acid) of at least about 5,000 molecular weight, having no upper molecular weight, but normally being not more than ten million, more usually not more than about six hundred thousand. There will usually be different ranges depending upon whether an enzyme or an antigen is involved, with enzymes generally ranging from about 10,000 to 600,000 molecular weight, more usually 10,000 to 300,000 molecular weight and antigens ranging from 5,000 to $10^7$, usually from 20,000 to 600,000, and more usually from 25,000 to 250,000 molecular weight; and n is at least 1 and not more than the number of available amino group present in A, generally being on the average in the range of about 1 to the molecular weight of A divided by 1,500; for enzymes n will usually be in the range of 1 to 30, more usually in the range of 2 to 30 and preferably in the range of 2 to 12, while for antigens the range will generally be from about 1 to 500, usually 2 to 250 and preferably about 2 to 100, particularly with the middle molecular weight antigens.

The manner in which the linking group may be joined to the amino functions may be varied widely, including a single bond, a double bond, or an amido group, including the nitrogen and sulfur analogs thereof, e.g. amidine, urea, thioamide and thiourea. Single bonds may be achieved by employing an alkyl halide or by reductive amination of an oxocarbonyl. Double bonds may be achieved by employment of a Schiff's base, while amides and their analogs can be achieved by activated esters, acyl halides, anhydrides, isocyanates and thiosocyanates.

Preferred R groups will for the most part have the following formula:

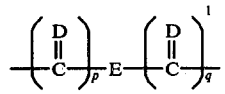

2.

wherein:
E is a bond, alkylene or alkyleneamino (the amino being terminal), wherein the alkylene is of from 1 to 5 carbon atoms, particularly 1 to 4 carbon atoms and preferably polymethylene;

D and $D^1$ are the same or different and are oxygen, nitrogen or sulfur, preferably oxygen, with —(C-D)— being bonded to the annular amino;

p and q are 0 or 1, the sum of p and q preferably being at least 1.

Illustrative R groups include carbonyl, maledioyl, succindioyl, glutardioyl, oxoethylene (—CH$_2$CO—), 1-oxopropylene-(—COCH$_2$CH$_2$—) and succindiiminoyl.

A compound of particular interest is the derivative of lidocane which has the following formula:

3.

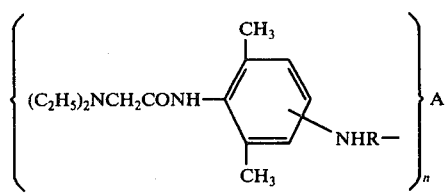

wherein:
R, A and n have been defined previously. Where the linkage involves a nonoxocarbonyl or its nitrogen and thio analogs thereof, the linking functionality will involve an amide, amidine or thioamide. For the most part, amides will be involved which will be linked to available amino groups on the antigen. Available amino groups will be present as the terminal amino group and with lysine, arginine, histidine, and the like.

The antigenic poly(amino acids) which may be used will vary widely as to molecular weight, normally being from about five thousand to ten million molecular weight, more usually from about twenty-five thousand to six hundred thousand molecular weight, and preferably from about twenty-five thousand to two hundred fifty thousand molecular weight.

Usually, there will be not more than about one conjugate per 1,500 molecular weight of the antigen, more usually not more than about one conjugate per 2,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from about 1 to 10, usually in the range of 2 to 5.

Various protein types may be employed as the antigenic material. These types include albumins, serum proteins, e.g. globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups e.g. lysines.

In preparing the subject compositions, an appropriate aniline derivative with the amino group protected is conveniently nitrated, so as to provide the meta- or para-nitroaniline. The protective group may then be removed from the amino group. The amino group is then appropriately acylated to provide the desired anilide, followed by reduction of the nitro to amino to provide the amino functionality for linking. The following formulii indicate the reaction sequence:

4.

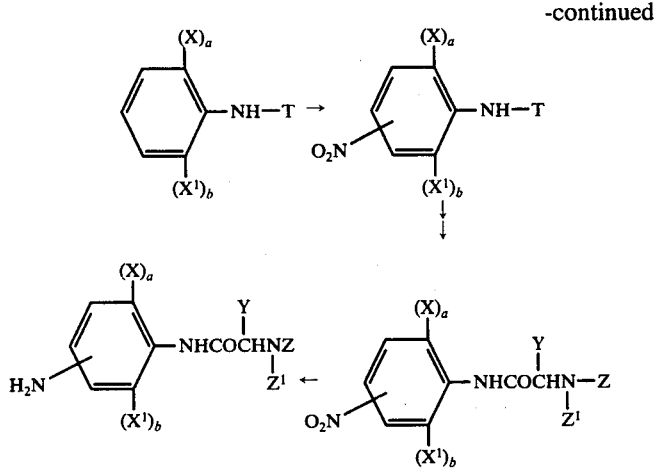

wherein:
all of the symbols have been defined except T, which is a protective group, such as arylsulfonyl, trifluoroacetyl or the like. Nitration is readily carried out in the presence of acid, with a weak carboxylic acid providing the para-derivative, while a strong mineral acid e.g. sulfuric acid provides the meta derivative. Temperatures in the range of about 50° to 100° C are employed.

The protective group is then removed by hydrolysis, conveniently by aqueous acid followed by acylation of the amino group with the appropriate amino acid or with chloroacetyl chloride, followed by displacement of the chloro with the appropriate secondary amine. The nitro group may then be reduced by any convenient means, for example catalytic hydrogenation, employing platinum or palladium under mold conditions, or other conventional reductant system.

The amino group derived from the nitro group may then be coupled using an active halogen, an activated acyl group, such as an active ester e.g. p-nitrophenyl, N-oxysuccinimide, etc., an acyl halide, an anhydride, or the carboxylic acid with a diimide, or condensation with a oxocarbonyl followed by reduction with a metal hydride. Usually, the second functionality on the linking group will be a nonoxocarbonyl, including the nitrogen and sulfur analogs thereof, which may be activated by any of the means indicated previously. The condensation of the antigen will normally be carried out under mild conditions generally from about −10° to 30° C in an inert polar solvent, usually a mixed aqueous solvent, which may have from about 0 to 50 volume percent of an organic solvent, such as a polyether, dimethylformamide, or the like. Generally, the reaction will be carried out at a pH in the range of about 7 to 10.

As previously indicated the antibodies find particular use in competitive protein binding assays. One competitive protein binding assay involves the use of enzyme conjugates and is referred to as a homogeneous enzyme immunoassay. In this assay, the enzyme is conjugated to a derivative of the compound of interest, whereby the resulting enzyme conjugate can be used in the immunoassay. Preferably, when antibody is bound to the groups conjugated to the enzyme, the enzyme undergoes a substantial change in its activity, usually a substantial diminution in its activity.

Normally, the number of groups conjugated to the enzyme will range from about 1 to 30, more usually from about 2 to 20, and preferably from about 2 to 12.

Various enzymes may be employed, such as oxidoreductases, hydrolases, lyases, and the like. Groups of particular interest include those enzymes which employ nicotinamide, adenine, dinucleotide (NAD) or its phosphate (NADP) as an acceptor, such as the dehydrogenases, including glucose 6-phosphate dehydrogenase, malate dehydrogenase, alcohol dehydrogenase, lactate dehydrogenase, and the like; peroxidases; oxidases; glycoside hydrolases; and the like.

For the most part, the enzyme conjugates will have the following formula:

5.

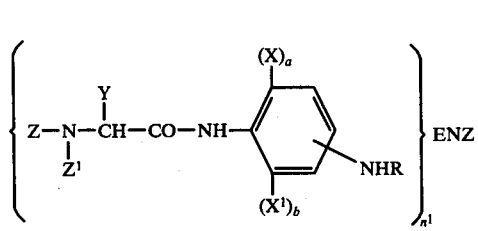

wherein:
all of the symbols have been defined previously except for $n^1$ which will be on the average from about 1 to 20, more usually from about 2 to 12; and
ENZ which intends enzyme. For the most part, the enzyme will have a molecular weight in the range of about 10,000 to 600,000, more usually from about 10,000 to 300,000. Illustrative enzymes other than those specifically set forth previously include lysozyme, β-glucuronidase, glucose oxidase, catalase and peroxidase.

A description of the method for carrying out the homogeneous enzyme immunoassay may be found in U.S. Pat. No. 3,817,837. The method involves combining the enzyme conjugate, the unknown sample suspected of containing the drug of interest and antibody for the drug of interest in an aqueous buffered medium and determining the enzymatic activity over a predetermined period of time as compared to a sample assay containing a known amount of the drug of interest.

The following examples are offered by way of illustration and not by way of limitation.

(All temperatures not otherwise indicated are centrigrade. All percents not otherwise indicated are by weight.) The following abbreviations find use:

(TLC-thin layer chromatography; DMF-dimethyl formanide; LAH - lithium aluminum hydride; THF - tetrahydrofuran)

EXAMPLE 1 p-Toulenesulphonamide of 2,6-dimethylaniline

To a solution of 16 ml (15.6g, 130mmoles) of 2,6-dimethylaniline in 50ml of seive-dried pyridine was added 27g (71 mmoles) of twice-recrystallized (hexane) tosylchloride. After heating at reflux for 2 hr., the reaction mixture was poured into 500ml of ice-cold 2N HCl, whereupon a yellow solid formed, which, after chilling in an ice bath, was collected, pressed with a rubber dam, and dried in vacuo over $P_2O_5$ for 1hr. (m.p. 130°–132°). The crude product was used as such for the next step.

EXAMPLE 2

Preparation of 1-(p-toluenesulphonylamino)-2,6-dimethyl-4-nitrobenzene

The crude sulphonamide of Ex. 1 was added in portions to 25ml of fuming nitric acid in 200ml of water: after the addition of 200ml of glacial acetic acid and ca. 700mg of $NaNO_2$, the mixture was refluxed for 1hr. With rapid stirring, the cooled mixture was poured into 400ml of ice water. The light yellow precipitate so formed was collected, washed with water, and dried in vacuo overnight to give 31.9g of the product (m.p. 157 –160°) that was >95% pure by TLC and NMR, an overall yield of 81% based on 2,6-dimethylaniline.

A sample was crystallized from ethanol-water, m.p. 162.5°–164°.

EXAMPLE 3

Preparation of 1-amino-2,6-dimethyl-4-nitrobenzene

The nitrosulphonamide, (Ex. 2) (31.9g. was suspended in a solution of 100ml of conc. $H_2SO_4$ and 10ml of water and heated in a water bath (~95°) and occasionally swirled until all material had dissolved. The resulting dark brown mixture was poured into 300ml of ice water and made basic (pH 12) with concentrated ammonium hydroxide. The resulting yellowish-brown precipitate was collected, washed with water, and crystallized from hot ethanol-water to give 11.3g of fine yellow needles (m.p. 156°–160°). Concentration of the mother liquor and addition of water gave 2.7g of the product, for a combined yield of 14g (82%). An analytical sample was cyrstallized from chloroform, m.p. 158°–159°.

EXAMPLE 4

Preparation of α-chloro-4-nitro-2,6-dimethylacetanilide

At room temperature, a solution of 6ml (76mmoles) of chloroacetylchloride in 30ml of seive-dried benzene was added dropwise to a rapidly stirring solution of 12g (72mmoles) of the product of Ex. 3 and 5.8ml (72mmoles) of dry pyridine in 500ml of benzene. A precipitate formed at once. Forty-five min. after the addition was completed, the reaction mixture was chilled, the precipitate collected, washed with water and dried in a vacuum desiccator overnight. Crystallization was achieved by dissolving the product in 2.5 1. of boiling benzene, which, after concentration to ca. 1.5 1. deposited the product (12.73g, 73%) as very long, thin light yellow needles, m.p. 227°–228°.

EXAMPLE 5

Preparation of α-diethylamino-4-nitro-2,6-dimethylacetanilide

The chloride of Ex. 4 (12.7g, 52.5mmoles) and 13.6ml of diethylamine (132mmole) in 75ml of dry benzene were refluxed for 15hr.; the chloride dissolved slowly, and the solution was clear at the end of the reaction.

After cooling, the brown solution was filtered and extracted thoroughly with 160ml of 10% hydrochloric acid. The combined aqueous layer was washed with ether, chilled and make alkaline with concentrated KOH, and the yellow precipitate was collected.

The product was dissolved in ethanol and crystallized from aqueous ethanol, first crop 9.7g, second crop 2.1g. for an 80% yield. The fluffy, light yellow crystals had a m.p. 92°–94°.

EXAMPLE 6

Prepartion of α-diethylamino-4-amino-2,6-dimethylacetanilide,

The nitro compound of Ex. 5 (2.0g, 7.2mmoles) in 50ml of ethanol, containing 20 drops of glacial acetic acid and two heaping spatulas of Adam's catalyst, was hydrogenated in a Parr apparatus at 35 lbs/in² for 2hr. The catalyst was filtered off under a nitrogen blanket with suction through a Celite pad, which was washed thoroughly with absolute ethanol. Evaporation gave a quantitative yield of a yellow oil that crystallized on standing.

The solid was dissolved in a minimum amount of ether, boiled with charcoal, concentrated, chilled and scratched to give two crops of fine yellow needles, 467 and 400mg respectively, m.p 91°–93°. A second crystallization from cyclohexane gave m.p. 93.5°–95°.

EXAMPLE 7

Preparation of the p-nitrophenyl ester of the carboxyamide of γ-diethylamino-4-amino-2,6-dimethylacetanilide and its conjugation to bovine γ-globulin (BgG)

To a solution of 55mg (0.22mmoles) of p-aminolidocaine (Ex. 6) in 2.0ml dry DMF under nitrogen was added 110μl of triethylamine. The solution was cooled to −20° and 53mg (0.26mmoles) of p-nitrophenylchloroformate added; the resulting mixture was stirred for 2 hrs between −10 and 20°. Over a period of 1 hr., the carbamate solution was added to 700mg of BgG (0.32mmole lysine) in a mixture of 30ml 0.1 M carbonate buffer (pH 9.1) and 12ml of DMF; the pH was constantly adjusted with HCl to maintain a value of 8–9. After complete addition of the carbamate, the reaction mixture was stirred in an ice bath for 3hrs., then dialyzed for ca. 3 days against 4×4 1. of 0.1 M NaHCO$_3$ and 4×4 1. of aqueous ammonium hydroxide, pH 9.

The conjugate solution was filtered through glass wool, then through a coarse fitted disk, and finally lyophilized to give 320mg of conjugate. The hapten number of 38.1 was determined by a u.v. difference technique at $\lambda_{max}$ 280nm.

EXAMPLE 8

Preparation of the hemisuccinamide of p-aminolidocaine

A solution of 1.54g (5.1mmoles) p-aminolidocaine (Ex. 6) and 520mg (5.2mmoles) of succinic anhydride in 50ml of dry THF (freshly distilled from LAH) was stirred over night. TLC (alumina, chloroform) showed starting material remaining. Small portions of the anhydride were added until TLC showed no starting material remained. The solvent was removed in vacuo to yield a yellowish foam.

The product was dissolved in water and 6N hydrochloric acid was added to pH 2, then the solution was evaporated to dryness. The residue was dissolved in a small amount of water and acetone was added, with heating, to the cloud point. The hydrochloride crystallized as small hexagonal crystals, m.p. 152°–154°. The material is very hygroscopic.

EXAMPLE 9

Conjugation of the hemissucinamide of p-aminolidocaine to BgG

Under nitrogen, 94mg (0.242mmoles) of the hemisuccinamde of p-aminolidocaine of Ex. 8 in 10ml dry DMF were treated with 68µl. (2eq) of triethylamine. After cooling to −25° and stirring for 30min., 32µl (leq) of isobutylchloroformate was added; stirring at −25° was continued for 1.5hrs.

The mixed anhydride prepared above was added dropwise in 15min. to an ice-cold solution of BgG (500mg, 0.242mmole lysine) in 20ml of water, pH 8.5. Dilute sodium hydroxide was added on demand to keep the pH between 8.4–8.7. The mixture was stirred for 2hr., then dialyzed once against 4 l. of 0.1M NaHCO$_3$ and against 4×4 l. of water. Lyophilization gave 300mg of conjugate.

A hapten number of 4.5 was determined by a u.v. difference technique at $\lambda_{max}$ 280nm.

A second conjugation following the above procedure gave a hapten number of 10.

EXAMPLE 10

Conjugation of the hemisuccinamide of p-aminolidocaine to bovine serum albumin (BSA)

The isobutyl mixed anhydride was prepared under nitrogen at −25° from 200mg of the hemisuccinamide of p-aminolidocaine of Ex. 8, 2 equivalent of triethylamine and 1 equivalent of isobutylchloroformate in 4ml of dry DMF. After 2hrs at −25°, the mixed anhydride was added to 300mg of BSA in 20ml of water, pH 8.5, at 0°, with dilute sodium hydroxide added on demand to keep the ph between 8.4 and 8.6.

The reaction mixture was stirred overnight, then dialyzed against 4 l. of 0.1M Na$_2$CO$_3$/0.1M NaHCO$_3$ buffer, and against several changes of water. Lyophilization gave 333mg of white powder.

A hapten number of 13 was found by using a u.v. difference technique at $\lambda_{max}$ 279 and 248nm.

EXAMPLE 11

Preparation of 1-benzenesulphonylamino-2,6-dimethyl-3-nitrobenzene

The crude sulphonamide of Ex. 1 (36.8g, 141mmoles) was suspended in a mixture of 250ml of glacial acetic acid and 120ml of concentrated sulphuric acid; the solution was warmed to 60°–70° and turned yellow. After cooling to ca. 45°, a solution of 50ml conc. sulfuric acid, 50ml glacial acetic acid, and 8ml of fuming nitric acid was added dropwise with vigorous stirring to the suspension, which was then stirred overnight at ambient temperature.

The resulting yellow slurry was poured onto 500g of ice, chilled, and collected. Crystallization from aqueous ethanol gave 32.2g of product, m.p. 130°–132°.

EXAMPLE 12

Preparation of 2,6-dimethyl-3-nitroaniline

The sulphonamide of Ex. 11, (32.2g 0.105moles), was suspended in 75ml of 90% sulphuric acid and heated on a steam bath for 20–30min., cooled, and poured into 300ml of ice water. The solid material which formed was filtered off by passing the solution through a cotton plug, and the resulting solution was chilled and made alkaline with concentrated ammonia. The yellow precipitate was collected and crystallized from benzene-light petroleum to give two crops weighing 14.2g (81%), m.p. 70°–72°. A second crystallization from benzene-heptane gave m.p. 72°–75°.

EXAMPLE 13

Preparation of α-chloro-3-nitro-2,6-dimetylacetanilide

With virgorous stirring, 4.4ml (7.21g. 55mmoles) of chloroacetylchloride in 50ml of dry benzene was added dropwise to 8.3g (50mmoles) of 2,6-dimethyl-3-nitroaniline in 200ml of dry benzene containing 4.1ml (50mmoles) of dry pyridine. Stirring was continued for 30min., and the yellow precipitate formed was collected, washed with water, and dried in a vacuum dessicator overnight. The product, fine needles, weighed 8.7g (72%), m.p. 162°–163°.

EXAMPLE 14

Preparation of α-diethylamino-3-nitro-2,6-dimethylacetanilide

A solution of 5.0g (20.6mmoles) of the chloro compound of Ex. 13 and 5.3ml (3.78g, 51.6mmoles) of diethylamine in 300ml of benzene was refluxed overnight. After cooling, the organic layer was extracted with three 50ml portions of 10% hydrochloric acid; the combined aqueous layer was washed with 50ml of benzene.

The aqueous layer was chilled and made alkaline with concentrated sodium hydroxide. No precipitate formed.

Extraction of the aqueous layer with 150ml of chloroform, followed by drying and evaporation, gave a yellow oil that solidified on standing (5.17g, 90%), m.p. 55°–59°.

By following the procedures of Exs. 6, 7, 9, and 10, the meta-nitrolidocaine can be reduced and conjugated to a variety of antigens for the preparation of antibodies to lidocaine.

EXAMPLE 15

Glucose-6-phosphate dehydrogenase conjugate to the hemisuccinamide of para-aminolidocaine A stock solution of glucose-6-phosphate dehydrogenase (G6PDH) was prepared by reconstituting a dry powder of G6PDH with 0.055M tris-HCl buffer, pH 8.1 (room temperature) to provide a concentration of about 2–3mg/ml. To a small flask was introduced 1ml of the enzyme solution and the solution cooled to 0° with stirring. To the solution was then added 20mg glucose-6-phosphate and 20mg NADH, followed by the slow addition of 300µl carbitol and the pH adjusted to 9 with 2N NaOH.

A solution was prepared of dry lidocaine hemisuccinamide HCl (0.075mmoles) in 375µl of dry DMF, the mixture stirred and 21µl of triethylamine added under the surface of the liquid with stirring, while maintaining the mixture at −10°. To the solution was slowly added 14μl of carbitol chloroformate under the surface of the stirred solution. After 1.5 hours and mixed anhydride was ready for use.

Over an interval of approximately 15sec, 25μl of the mixed anhydride was added under conditions to minimize local concentrations. After approximately a 15 minute reaction time, an aliquot of the enzyme was removed and checked for activity and the addition of the mixed anhydride repeated as described above until the desired activity and inhibitability was obtained. The pH is maintained above 8.5 during the course of the reaction by the addition of 2N sodium hydroxide as required. The following table indicates the results obtained. The assays were carried out with antibodies prepared in response to injection of the antigen of Ex. 9 in accordance with conventional procedures. The assay procedure will be described subsequently.

TABLE I

| Run No | Content[1] | pH | Corrected ΔOD | Conjugation Volume ml | %I[2] | %D[3] | Total[4] M.A. added |
|---|---|---|---|---|---|---|---|
| 1 | Enzyme Carbitol | 9.04 | 745[5] | 1.31 | — | — | — |
| 2 | 1 + 25μl MA | 9.00 | 725 | 1.335 | 7.9 | 3.2 | 25 |
| 3 | 2 + 50μl MA | 8.97 | 681 | 1.385 | 16.1 | 9.0 | 75 |
| 4 | 3 + 50μl MA | 8.94 | 626 | 1.435 | 27.9 | 16.5 | 125 |
| 5 | 4 + 100 μl MA | 8.90 | 553 | 1.535 | 57.5 | 23.1 | 225 |
| 6 | 5 + 50μl MA | 8.89 | 495 | 1.585 | 69.6 | 34.0 | 275 |
| 7 | 6 + 50μl MA | 8.88 | 432 | 1.635 | 81.4 | 42.4 | 325 |
| 8 | 7 + 50μl MA | 8.87 | 310 | 1.685 | 93.5 | 58.6 | 375 |

[1] Indicates content of reaction mixture with each run having an additional amount of MA added to the mixture and a 5 μl aliquot taken for testing.
[2] % Inhibitability refers to reduction in rate in presence of excess anti(lidocaine)
[3] % Deactivation is the loss of enzyme activity due to conjugation of the lidocaine derivative
[4] MA intends mixed anhydride It is evident from the above table that excellent inhibitability can be achieved, while still having a relatively low degree of deactivation. Thus, the enzyme conjugates can be used in assays for the determination of lidocaine, where relatively large differences in optical density can be read over relatively short periods of time based on small differences in the concentration of lidocaine in the assay medium.

In carrying out the assay, a Gilford 300N Micro-sample Spectrophotometer is employed, with a Thermocuvette with a flow cell. All readings are made at 340 nm. The following solutions are prepared as reagents for use in the assay:

TABLE II

| | |
|---|---|
| Buffer: | 0.055 M tris-HCl, pH 8.1 (RT) |
| | 0.05% sodium azide |
| | 0.005% Thimerosal |
| Enzyme conjugate: | Buffer |
| | 0.9% NaCl |
| | 1.0% RSA, pH 8.1 (RT) |
| | sufficient enzyme conjugate (Ex. 15) |
| | to give a maximum rate of ΔOD equal to 750 |
| | in the essay medium. |
| Assay Buffer: | Buffer |
| | 0.5% NaCl |
| | 0.01% (v/v) Triton X-100, pH 8.1 (RT) |
| Antibody Reagent | Buffer |
| | 1.0% RSA |
| | G6P(Na) 0.066M |
| | NAD 0.04M |
| | pH 5(RT) |
| | antilidocaine optimized for assay |
| | All % unless otherwise indicated are w/v (g/ml) |
| | RSA-rabbit serum albumin |

The protocol employed for carrying out an assay is as follows. 50μl of the sample is drawn up into a diluter and dispensed with 250μl of the assay buffer into a 1ml Croan cup. A 50μl aliquot of the diluted sample is drawn up and dispensed with a 250μl portion of assay buffer into a second Croan cup. Into the second Croan Cup is introduced 50μl of the antibody reagent with 250μl of the assay buffer, followed by the addition of 50μl of the enzyme reagent and 250μl of the assay buffer. Immediately after the enzyme addition, the entire sample is aspirated into the flow cell. After 15sec. a first reading is taken, followed by a second reading after a thirty second interval. The results are reported as the difference in absorbance ×2.667.

The following table indicates the results obtained with a number of samples having known amounts of lidocaine.

TABLE III

| Lidocaine Conc. in Sample μg/ml | ΔODx 2.667 |
|---|---|
| 0 | 282 |
| 1 | 321 |
| 2 | 364 |
| 3 | 392 |
| 5 | 434 |
| 12 | 487 |

By graphing the above results on semilog paper, one can then determine the concentration of lidocaine in a sample suspected of containing lidocaine.

A cross-reactivity study was carried out where samples were spiked with 3μg/ml. of lidocaine serum and μl of the cross-reactant. No cross-reactivity was observed with such closely similar drugs as procainamide, isoproterenol, propranolol, ephedrine, and methamphetamine.

Of the known metabolites of lidocaine, monethylglycinexylidide and glycinexylidide, only the former showed some cross-reactivity. However, it was found that by introducing amounts of this cross-reacting metabolite in the range of about 3 to 10 μg/ml into the assay medium, the cross-reactivity could effectively be damped, so that any of the metabolite present in the sample to be assayed would not significantly affect the reading.

It is evident from the above results, that a sensitive accurate reproducible assay for lidocaine and lidocaine analogs is achievable in accordance with this invention. Antibodies which are produced do not show significant cross-reactivity, except with the desethyl metabolite of lidocaine. This cross-reactivity is easily removed by adding a small amount of the metabolite to the assay medium, so that any additional amounts of the metabolite present in the sample to be assayed do not affect the result.

Although the foregoing invention has been described in some detail by way of illustration and example for purposes of clarity of understanding, it will be obvious that certain changes and modifications may be practiced within the scope of the appended claims.

What is claimed is:

1. A composition of the formula

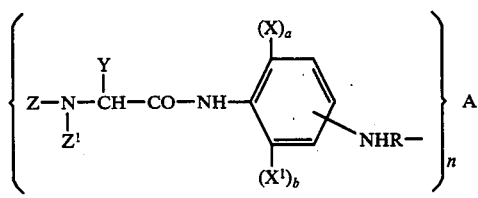

wherein:
X and $X^1$ are methyl;
$a$ and $b$ are 0 or 1, the sum of $a + b$ being at least 1;
Y is hydrogen, methyl, or may be taken together with Z to form a 6 membered ring with the carbon and nitrogen atoms to which Y and Z are respectively attached;
Z and $Z^1$ are the same or different and are alkyl of from 1 to 4 carbon atoms, with the proviso that Z may be taken together with Y;
the amino groups bonded to the aromatic ring are separated by from 3 to 4 carbon atoms;
R is a linking group;
A is a poly(amino acid) of at least about 5,000 molecular weight; and
$n$ is at least 1 and not more than the number of available amino groups present in A.

2. A composition according to claim 1, wherein A is an antigen.

3. A composition according to claim 1, wherein A is an enzyme.

4. A composition according to claim 1, wherein Z and $Z^1$ are ethyl, $a$ and $b$ are both 1 and Y is hydrogen.

5. A composition according to claim 1, wherein R is of the formula

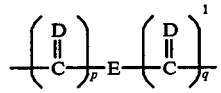

wherein:
E is a bond, alkylene or alkyleneamino of from 1 to 5 carbon atoms;
D and $D^1$ are oxygen, nitrogen or sulfur; and $p$ and $q$ are 0 or 1.

6. A composition according to claim 5, wherein E is alkylene $p$ and $q$ are 1 and D and $D^1$ are oxygen.

7. A composition according to claim 5, wherein $p$ is 1, $q$ is 0 and E is a bond.

8. A composition of the formula

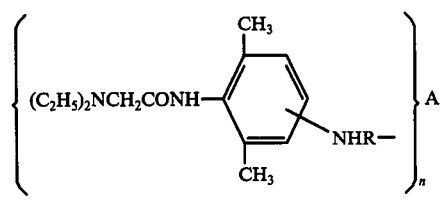

wherein:
A is a poly(amino acid);
$n$ is is the range of 1 to 500;
R is of the formula

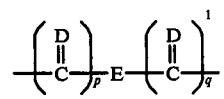

wherein:
E is a bond, alkylene or alkyleneamino of from 1 to 5 carbon atoms;
D and $D^1$ are oxygen or nitrogen; and
$p$ and $q$ are 0 or 1.

9. A composition according to claim 8, wherein A is an antigen.

10. A composition according to claim 8, wherein A is an enzyme.

11. A composition according to claim 8, wherein D and $D^1$ are oxygen, and $p$ and $q$ are 1.

12. A composition according to claim 11, wherein E is alkylene.

13. A composition according to claim 8, wherein E is a bond, $D^1$ is oxygen, $q$ is 1, and $p$ is 0.

14. A composition of the formula

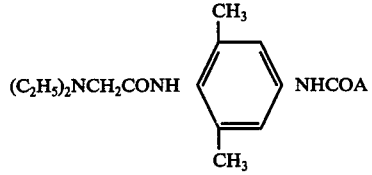

wherein:
A is a poly(amino acid).

15. A composition according to claim 14, wherein A is bovine γ-globulin.

16. A composition of the formula

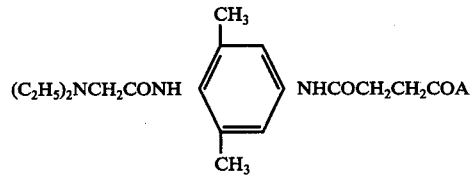

wherein:
A is an antigenic poly(amino acid).

17. A composition according to claim 16, wherein A is bovine γ-globulin.

18. A composition according to claim 16, wherein A is bovine serum alubmin.

19. A composition of the formula

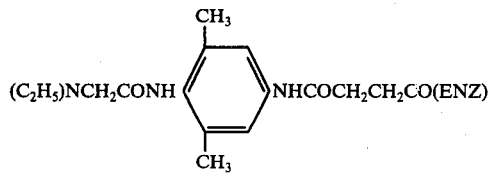

wherein:
ENZ is an enzyme.

20. A composition according to claim 19, wherein said enzyme is a dehydrogenase.

21. A composition according to claim 20, wherein said dehydrogenase is glucose-6-phosphate dehydrogenase.

22. An antibody prepared in response to a conjugate according to claim 2.

23. An antibody prepared in response to a conjugate according to claim 9.

24. An antibody prepared in response to a conjugate according to claim 16.

* * * * *